(12) United States Patent
O'Donnell (10) Patent No.: US 8,128,552 B2
(45) Date of Patent: Mar. 6, 2012

(54) SURGICAL INSTRUMENT FOR TREATING FEMALE PELVIC PROLAPSE

(76) Inventor: Pat D. O'Donnell, Springfield, IL (US)

( * ) Notice: Subject to any disclaimer, the term of this patent is extended or adjusted under 35 U.S.C. 154(b) by 1678 days.

(21) Appl. No.: 11/209,021

(22) Filed: Aug. 22, 2005

(65) Prior Publication Data

US 2007/0043255 A1 Feb. 22, 2007

(51) Int. Cl.
*A61F 2/02* (2006.01)
(52) U.S. Cl. ........................................................ 600/30
(58) Field of Classification Search ................. 128/885, 128/898; 600/29–30, 32, 37; 623/11.11, 623/13–14, 16–17, 23
See application file for complete search history.

(56) References Cited

U.S. PATENT DOCUMENTS

| | | | |
|---|---|---|---|
| 4,052,988 A | 10/1977 | Doddi et al. | |
| 4,441,496 A | 4/1984 | Shalaby et al. | |
| 4,564,013 A | 1/1986 | Lilenfeld et al. | |
| 4,979,956 A * | 12/1990 | Silvestrini | 623/13.11 |
| 5,112,344 A | 5/1992 | Petros | |
| 5,486,197 A | 1/1996 | Le et al. | |
| 5,578,046 A | 11/1996 | Liu et al. | |
| 5,626,611 A | 5/1997 | Liu et al. | |
| 5,686,090 A | 11/1997 | Sc-hilder et al. | |
| 5,720,753 A | 2/1998 | Sander et al. | |
| 5,720,766 A | 2/1998 | Zang et al. | |
| 5,725,541 A | 3/1998 | Anspach, III et al. | |
| 5,895,396 A | 4/1999 | Day et al. | |
| 5,899,909 A | 5/1999 | Claren et al. | |
| 5,968,078 A | 10/1999 | Grotz et al. | |
| 5,997,554 A * | 12/1999 | Thompson | 606/148 |
| 6,031,148 A | 2/2000 | Hayes et al. | |
| 6,039,686 A * | 3/2000 | Kovac | 600/30 |
| 6,042,534 A | 3/2000 | Gellman et al. | |
| 6,042,536 A * | 3/2000 | Tihon et al. | 600/37 |
| 6,093,200 A | 7/2000 | Liu et al. | |
| 6,096,060 A | 8/2000 | Fitts et al. | |
| 6,200,330 B1 | 3/2001 | Benderev et al. | |
| 6,273,852 B1 | 8/2001 | Lehe et al. | |
| 6,315,788 B1 | 11/2001 | Roby | |
| 6,319,270 B1 | 11/2001 | Grafton et al. | |
| 6,334,446 B1 * | 1/2002 | Beyer | 128/898 |
| 6,355,066 B1 | 3/2002 | Kim | |
| 6,387,041 B1 | 5/2002 | Harari et al. | |
| 6,406,423 B1 | 6/2002 | Scetbon | |
| 6,506,190 B1 * | 1/2003 | Walshe | 606/139 |
| 6,544,273 B1 | 4/2003 | Herari et al. | |
| 6,551,343 B1 | 4/2003 | Tormala et al. | |
| 6,689,047 B2 * | 2/2004 | Gellman | 600/30 |
| 6,692,499 B2 | 2/2004 | Tormala et al. | |
| 6,808,486 B1 * | 10/2004 | O'Donnell | 600/30 |
| 6,908,425 B2 * | 6/2005 | Luscombe | 600/30 |
| 6,960,160 B2 * | 11/2005 | Browning | 600/37 |

(Continued)

*Primary Examiner* — Samuel Gilbert
(74) *Attorney, Agent, or Firm* — Winstead P.C.

(57) ABSTRACT

A surgical instrument for treating female pelvic prolapse comprising a mesh sling for implanting into the pelvis of a female, which provides support to the urethra, the anterior vaginal wall, and the posterior vaginal wall with the sling defining a tissue-anchoring segment attached to opposite ends of the mesh sling. The mesh sling is surgically positioned using a tissue anchor applier instrument. The tissue anchor segment is positioned to attach to durable fascia that is located anatomically to support the sling. The durable fascia anchored vaginal wall support sling is positioned to provide support to the urethra for surgical management of female urinary incontinence, support to the anterior vaginal wall for surgical management of female cystocele, and support to the posterior vaginal wall for surgical management of female rectocele.

13 Claims, 12 Drawing Sheets

U.S. PATENT DOCUMENTS

| | | |
|---|---|---|
| 7,070,556 B2 * | 7/2006 | Anderson et al. ............... 600/29 |
| 7,285,086 B2 * | 10/2007 | Smith et al. ..................... 600/30 |
| 2002/0019649 A1 | 2/2002 | Sikora et al. |
| 2002/0072806 A1 | 6/2002 | Buskirk et al. |
| 2002/0169452 A1 | 11/2002 | Tormala et al. |
| 2002/0188301 A1 | 12/2002 | Dallara et al. |
| 2003/0191360 A1 | 10/2003 | Browning |
| 2004/0044364 A1 | 3/2004 | DeVries et al. |
| 2004/0138705 A1 | 7/2004 | Heino et al. |
| 2006/0089525 A1 * | 4/2006 | Mamo et al. .................... 600/37 |

* cited by examiner

Fig. 12

SURGICAL INSTRUMENT FOR TREATING FEMALE PELVIC PROLAPSE

CROSS REFERENCE

This application does not claim priority from any prior application.

STATEMENT OF FEDERALLY SPONSORED RESEARCH/DEVELOPMENT

This application is not federally sponsored research/development.

REFERENCES TO SEQUENCE LISTING

This application is not referenced to any microfiche appendix.

BACKGROUND OF THE INVENTION

The present invention relates to surgical instruments for treating female urinary stress incontinence, female cystocele, and female rectocele generally and in particular, implanting a mesh sling using fascia tissue anchors to secure the sling in position.

Urethral sling procedures have become widely used as the primary surgical procedure for treatment of stress incontinence in women. The complexity of surgical placement and technical difficulty with the anatomical positioning of the sling continues to be a problem for surgeons and patients.

Current minimally invasive sling procedures utilize a long sling material and instruments for placement of the sling that are passed through the lower abdomen or the obturator fossa of women. Residual mesh material extends to the skin of the lower abdomen when an abdominal approach is used and it extends to the skin near the labia in the trans obturator approach. The excess sling material that extends through the abdominal wall or the obturator fossa is a permanent material which remains a source for possible infection and discomfort for the remainder of the life of the patient.

A sling for treatment of urinary incontinence in women is needed that is less invasive with less risk for complications than is currently available. This is especially important for the high risk elderly woman who needs surgical management of urinary incontinence or vaginal vault prolapse. Improved surgical techniques are needed for placement of support materials for cystocele repair and rectocele repair. Current surgical techniques for placement of supporting materials in repair of cystocele and rectocele are technically difficult to secure in the correct anatomical position and do not have predictable results. A wide range of supporting materials are used by different surgeons. The different materials are usually cut to fit the perceived defect at the time of surgery and sutured in position. Classic suturing of support materials in position for cystocele repair and rectocele repair is technically difficult for the surgeon to accomplish because of compromised surgical exposure of the vaginal apex that occurs during surgery for prolapse in most patients. A surgical technique is needed that can allow the surgeon to accurately position supporting materials in the anterior vaginal wall for cystocele repair and in the posterior vaginal wall for rectocele repair.

BRIEF SUMMARY OF THE INVENTION

In the preferred embodiment of the present invention, a mesh sling is positioned anatomically for treatment of incontinence in women and held in position by fascial tissue anchors that are attached to durable pelvic fascia in women. The mesh sling for treatment of stress incontinence in women is positioned to support the mid urethral continence site. The mesh sling can provide support for the proximal urethral continence site and the bladder neck continence site. The mesh sling is anchored at each end by fascial tissue anchors into durable fascia of the pelvis. The pelvic fascia used for anchoring the sling includes any fascia or supporting structures attached to the bones of the pelvis. This includes the pubocervical fascia, the periurethral fascia, the urethropelvic ligament, the fascia of the obturator internus, the pelvic fascia and ligaments attached to or overlying the pelvis, and durable fascia of the pelvis attached to the sacrum.

The mesh sling may be a single layer, a tubular sling, or multilayered. The sling may contain a combination of mesh and tissue remodeling material. The sling material and the tissue anchor material may be biodegradable, non-biodegradable, or a combination of both. The sling material and the tissue anchor material may be organic (carbon containing) inorganic (non-carbon containing) or a combination of both. The mid-segment of the sling may be non-biodegradable and the distal segment biodegradable so that when the sling has adequate tissue ingrowth to secure the sling into position, the distal segment that provided initial support will disappear over time as a biodegradable segment. When tissue remodeling materials are used, the sling may provide support to the remodeling material until tissue regrowth has occurred and the remodeling material is securely in position. At that time, complete biodegradation of the sling and anchoring system may occur.

The tissue anchor pins project from the shaft of the anchors or from the body of the sling. Tissue anchor pins are S-shaped structures or triangular shaped structures that are attached to the shaft of the tissue anchor or to the surface of the sling. The tissue anchor pins have elongated sharp tips that penetrate the durable fascia of the pelvis for securing the tissue anchor and the sling into the correct anatomical position. The tissue anchor pins may be attached to the shaft of the tissue anchor or the surface of the sling alone without a tissue anchor attached to the end of the sling. The distal tissue anchoring segment of the sling may be circular or flat. It may be hollow for insertion of a deployment instrument. A deployment instrument can be used to place the anchoring tip of the sling into the durable fascia of the pelvis or bone tissue. A single tip deployment instrument is used to deploy one side of the sling at a time. A double tip deployment instrument is used to deploy both ends of the sling simultaneously. The tissue anchoring pins on each end of the sling anchor the ends of the sling into durable fascia of the pelvis.

In another embodiment, the distal segment of the sling is pulled into position using a sling transfer instrument placed through the lower abdomen or through the obturator fossa which results in anchoring the sling into durable fascia of the pelvis. The sling tip has a hook on the end of a string material attached to the tip of the sling or a narrow segment of the sling. The sling hook is engaged into the tip of the sling transfer instrument and the sling is placed in the correct anatomical position. The hook may be attached to a string at the tip of the sling or the hook may be attached to a continuation of the sling that is pulled through the lower abdomen or obturator fossa using the sling transfer instrument. Both biodegradable and non-biodegradable materials may be used as a combination mesh material or as segmental components of the sling such as the body of the sling being composed of non-biodegradable material and the distal segment being composed of biodegradable material. The distal segment of the sling can be transferred to the suprapubic area or to the lateral labial area through the obturator foramen using the sling transfer instrument. The sling is secured in anatomical position by the pins on the shaft of the tissue anchors. The tissue anchor pins may be located on the body of the sling to secure it into position.

In women who have a cystocele due to lateral vaginal wall defects or vaginal apical defects, conventional cystocele repair techniques have had poor long term success rates following repair. Conventional transvaginal repair of lateral vaginal wall defects is technically difficult to surgically accomplish. Specially designed suturing devices have been developed for placement of sutures into the arcus tendineus of the levator ani. Even with specially designed suturing devices, conventional suturing is technically difficult. The resulting anatomical position of the surgical placement of materials is unpredictable. When the sutures are tied using conventional surgical techniques, the supporting materials are often positioned incorrectly. Anatomical supporting materials can be positioned more accurately using tissue anchors because the deployment is easier and more accurate than using conventional suturing techniques. The cystocele sling repair is done using tissue anchors placed in durable fascia of the pelvis. The fascial placement of the tissue anchors includes anatomically durable fascia or ligaments of the female pelvis. The surgical repair of the vaginal apex is especially difficult to achieve using conventional surgical techniques. Attachment of the sling to the durable fascia of the sacrum using tissue anchors provides a secure fixation of the vaginal apex to the fascial of the sacrum. The sling design for repair of vaginal apex defects utilizes a uterosacral ligament reinforcement technique. Rectocele repair is done using a similar technique. The sling supporting material for vaginal prolapse is placed in anatomical position and secured in position using tissue anchors.

It is another object of the instant invention to utilize tissue anchor pins to secure a sling device in the correct anatomical position for surgical treatment of urinary incontinence in women.

A further object of the instant invention to utilize the durable fascia of the pelvis for anchoring of a supporting sling for surgical treatment of urinary incontinence in women.

Yet another object of the instant invention to utilize S-shaped and triangular shaped tissue anchor pins secure a supporting sling to the durable fascia and ligaments of the pelvis.

An additional object of the instant invention to place a supporting sling secured in anatomical position with tissue anchors using a sling transfer instrument that is passed through the lower abdomen or the obturator foramen.

It is also an object of the instant invention to utilize the durable fascia and ligaments of the pelvis for anchoring of a supporting sling for surgical repair of cystocele and rectocele in women.

BRIEF DESCRIPTION OF THE DRAWINGS

FIG. 2 is an illustration of an embodiment of the present invention's single handle sling and tissue anchor insertion tool.

FIG. 5 is an illustration of an embodiment of the present invention's cylindrical fascia tissue anchor with triangular shaped anchoring pins on the shaft of the anchor.

DETAILED DESCRIPTION OF THE INVENTION

While the making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the instant invention.

The claims and specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

Figure 1:
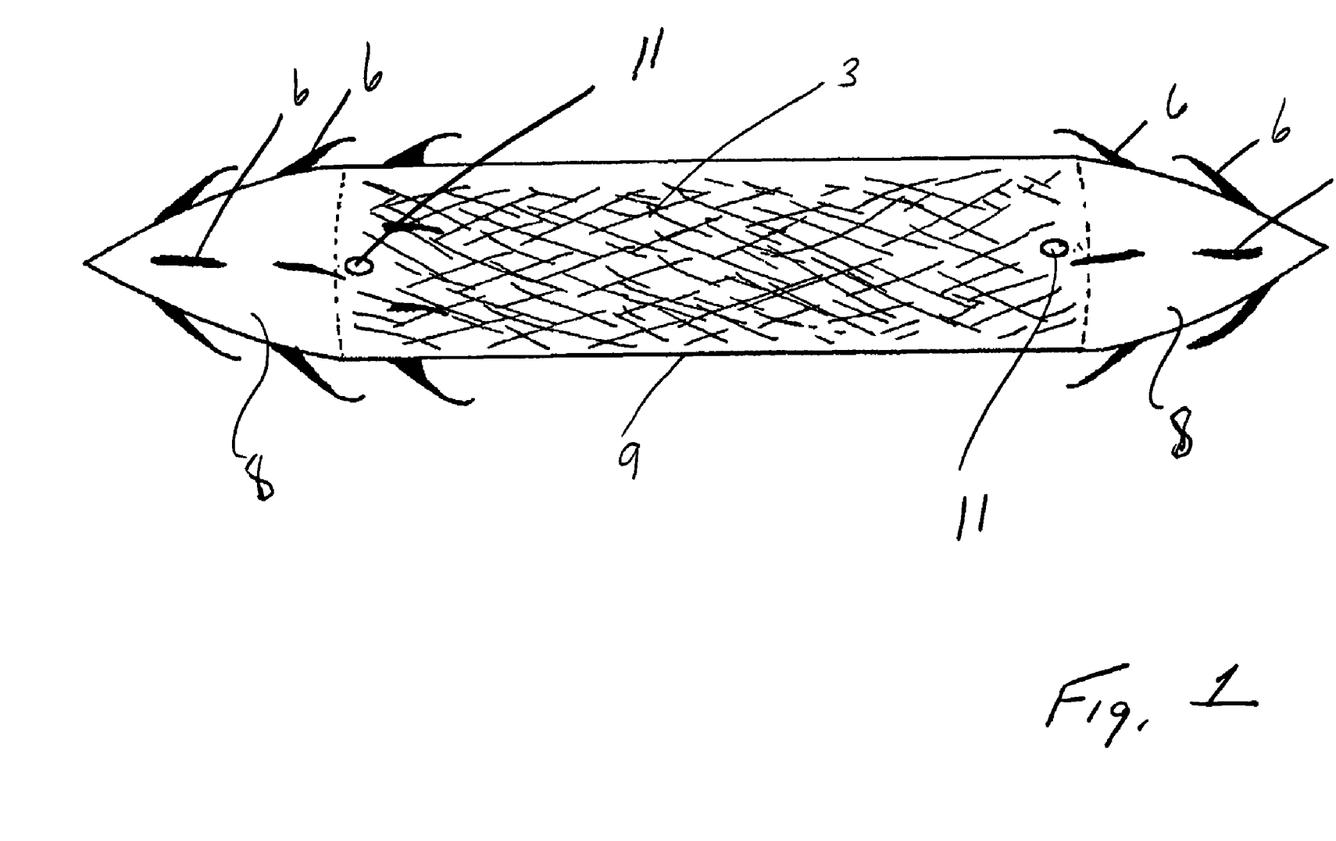
FIG. 1 is an illustration of an embodiment of the present invention's vaginal wall support sling with pelvic fascia tissue anchors positioned on each end of the sling.

Turning now to FIGS. 1-11 wherein the system, apparatus and methodology of the present invention is disclosed. It is to be noted that all dimensions and structural definitions provided herein are for purposes of illustration only to facilitate full and enabling disclosure. Such structural distinction/examples and dimensions are not to be considered limiting the scope of the present invention as those reasonably skilled in the relevant art who readily appreciate slight modifications thereto will not diminish the intent design and scope of the present invention. Turning now to FIG. 1.

In FIG. 1, the vaginal wall support sling of the present invention is illustrated. In defining practice, the sling of the invention is typically without limitation 1.5 centimeters in width. A range of 1.0 to 4.0 centimeters in width has been found to acceptably facilitate the practice of the present invention with a sling length of 6 centimeters and an acceptable range varying between but not limited to 3 cm to 12 cm.

The sling is comprised of a woven mesh material (3) 0.006 to 0.012 inches in diameter and may be structured in single or multiple layers. The mesh (3) utilized in the present invention sling may be composed of either biodegradable or non-biodegradable material or any chemical combination both in weave and segmental composition. The anchor pins (6) illustrated in FIG. 1 may be variably positioned on either the tissue anchor (8), the body of the sling (9) or on both the sling body (9) and anchor (8). The tissue anchor (8) may be round, square, rectangular, oval, spiral or flat in structure and the tissue anchor tip may be composed of a material similar or different from that of the sling and consist of a combination of any biodegradable or non-biodegradable material. As further illustrated in FIG. 1 the anchor tip (8) or sling body (9) may have an opening (11) through the center that may extend for any length for deployment using one or more embodiments of the inventions deployment/insertion tools.

FIG. 2 is an illustration of an embodiment of the present inventions single-handed sling and tissue anchor deployment tool. In FIG. 2, the deployment tool of the instant invention is illustrated having a tip design for inserting the anchoring portions (8) of the sling into durable fascia or ligaments of the pelvis. Also shown in FIG. 2 is the handle (16) and shaft portion (17) of the single tip deployment tool.

Figure 3:
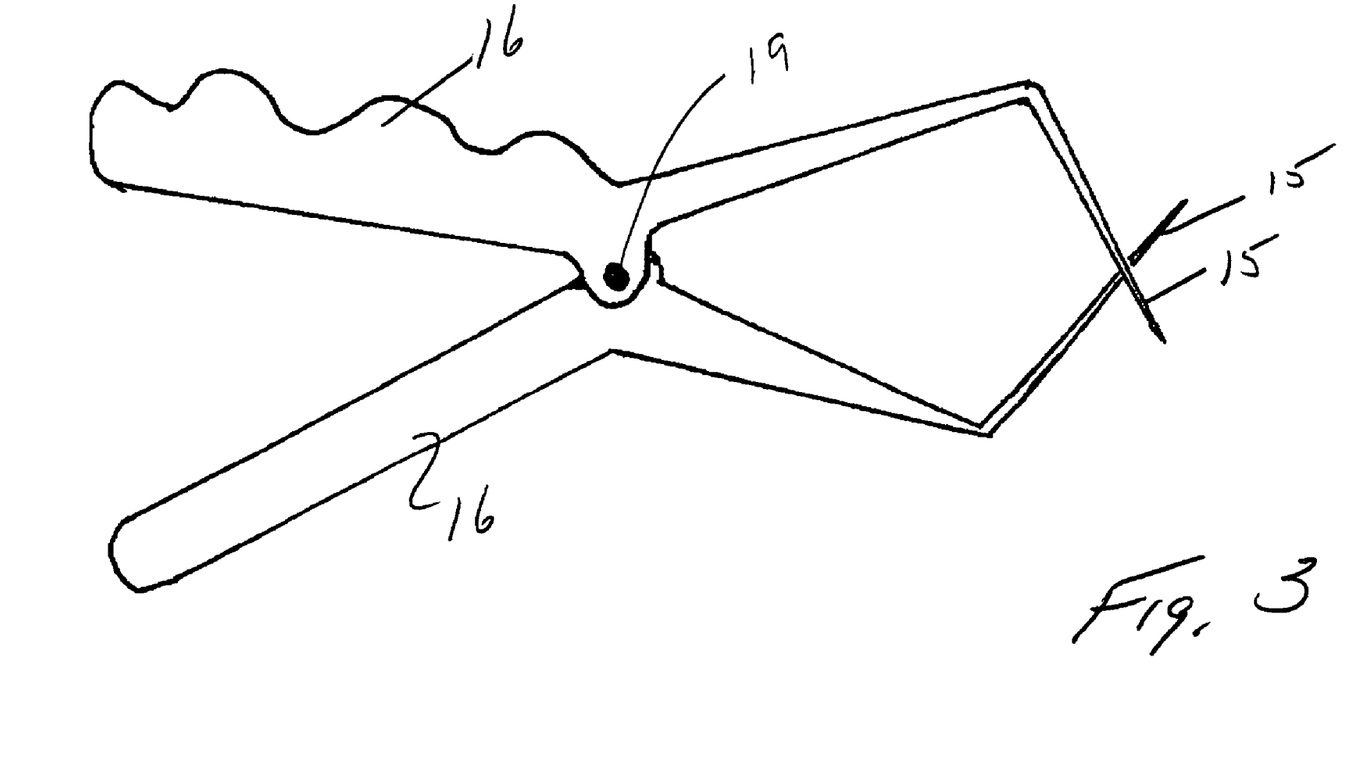
FIG. 3 is an illustration of an embodiment of the present invention's double handle sling and tissue anchor insertion tool.

In FIG. 3, an alternative embodiment of the insertion tool of the instant invention and is disclosed as a double handle sling tissue anchor insertion tool. FIG. 3 discloses the double handle insertion tool of the present invention as a pair of single handle deployment tools pivotally connected (19) and structured to allow for simultaneous insertion of both anchoring ends (8) of the sling into durable fascia or ligaments of the pelvis. As the handle portions (16) of the deployment tool are compressed or brought together the tip portions (15) extend in opposite directions to allow for secure/tight variably tension sling deployment and insertion.

Figure 4:
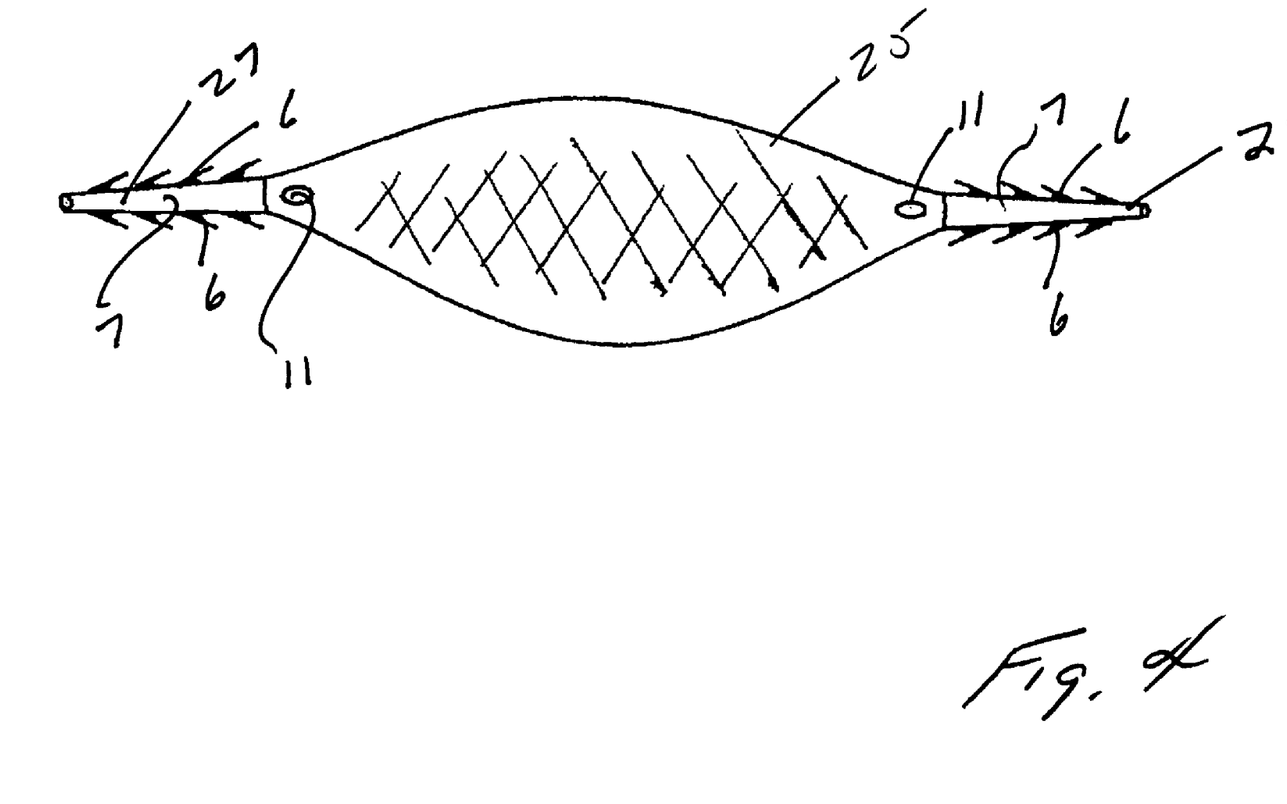
FIG. 4 is an illustration of an embodiment of the present invention's contoured sling with pelvic fascia tissue anchors on each end of the sling.

FIG. 4 illustrates an embodiment of the present invention's contoured sling with pelvic fascia tissue anchors on each end of the sling. In FIG. 4, a contoured sling (25) is shown attached to round tissue anchors (27) positioned on opposite ends of the sling. The tissue anchors shown and disclosed for full and enabling disclosure are hollow with triangular shaped anchoring pins (6) located on a tissue anchor shaft (7). As practiced, the tissue anchoring pins (6) are attached to the tip of the vaginal wall support sling. This embodiment of the sling is envisioned for, though not limited to use for surgical management of the female stress urinary incontinence and provides anatomical support to the mid urethra, the proximal urethra, bladder neck and base of the bladder. FIG. 4 further discloses one or more openings (11) in the body of the sling purposely positioned for placement and insertion of the tissue anchoring deployment tool as illustrated and discussed in association with FIGS. 2 and 3.

FIG. 5 illustrates a cylindrical fascia tissue anchor (12) with triangular shaped anchoring pins (6) on the shaft of the anchor (7). In FIG. 5 the fascia tissue anchor (12) is round and hollow to allow the invention's insertion tool to pass completely through the anchor. This particular embodiment allows the sharp tip (15) of the insertion tool to penetrate dense scar tissue to accurately place the support sling. The cylindrical fascia tissue anchor with triangular shape anchoring pins as illustrated in FIG. 5 may be utilized to attach the tissue anchor to the support sling at one or more sites at each end of the sling for securing the sling to durable fascia and ligaments of the pelvis. The sharp tip of the deployment tools discussed in association with FIGS. 2 and 3 allow for placement of this tissue anchor into dense scar tissue from previous surgery as well as ligaments and bone tissue.

Figure 6:
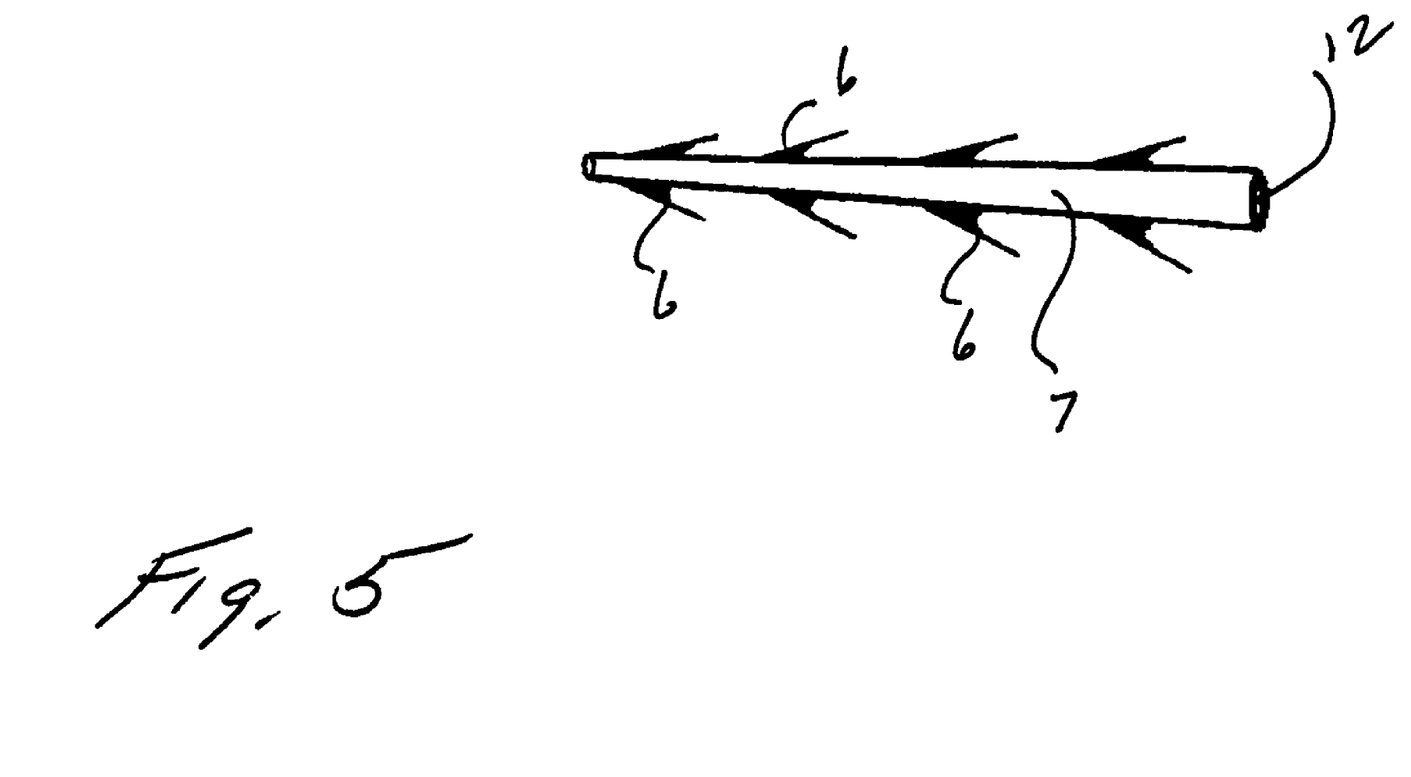
FIG. 6 is an illustration of an embodiment of the present invention's S-shaped fascia tissue anchoring pin.

FIG. 6 illustrates an S-shaped fascia tissue anchoring pins (30). This embodiment of the anchoring pin of the present invention attaches to the shaft (7) of the tissue anchor and the body of the sling (9). It has been contemplated that the anchoring pins may be located on the anchor only or the anchoring pins may be located on any part of the sling and the sling may further have anchoring pins positioned at any location on the sling with or without a tissue anchor on the tip of the sling. The elongated sharp tip (31) of the anchoring device as illustrated in FIG. 6 allows the tissue anchor (30) to be secured into tissues having different types of connective tissue such as fat, muscle, fascia and ligaments. The anchoring pin may be made of biodegradable material, non-biodegradable material organic material or inorganic material. It may further be of the same or different material than that of the anchor shaft or the body of the sling.

Figure 7:
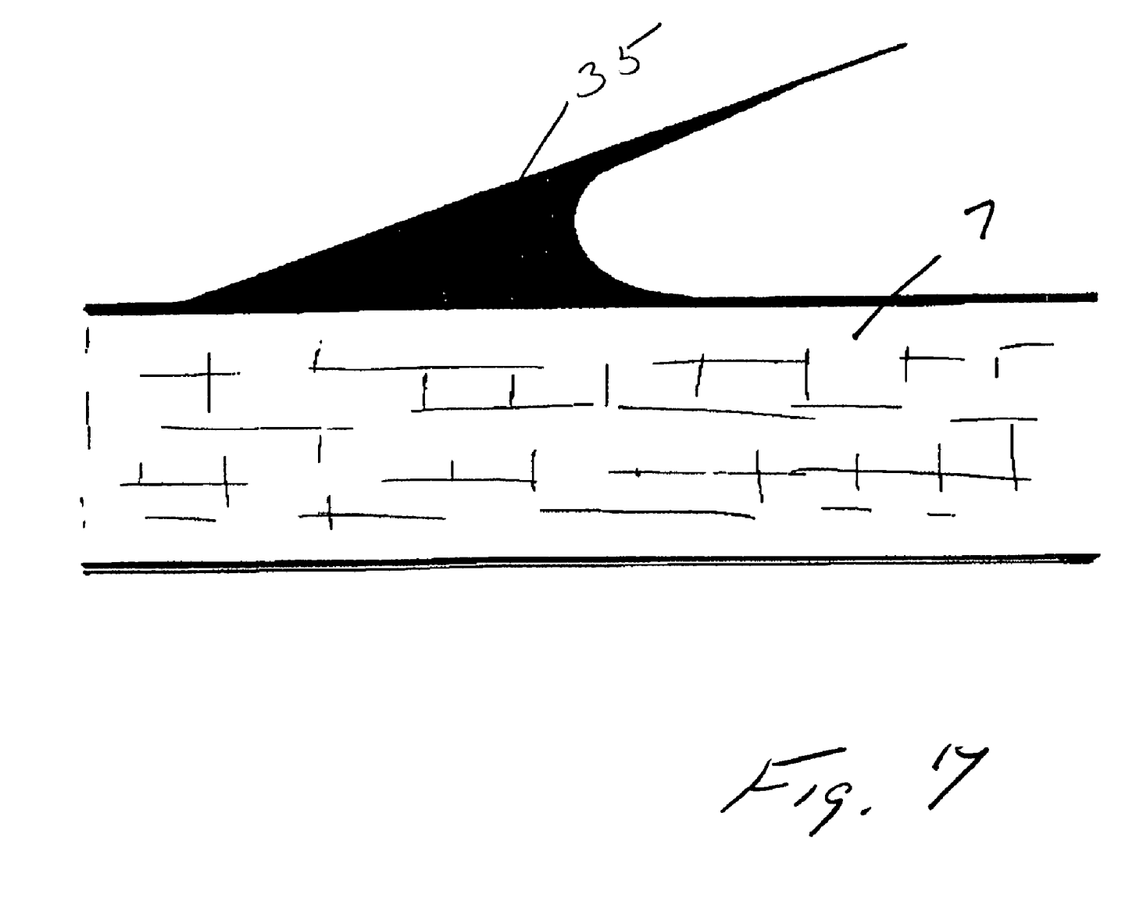
FIG. 7 is an illustration of an embodiment of the present invention's triangular shaped fascia tissue anchoring pin.

FIG. 7 illustrates an embodiment of a triangular shaped fascia anchor pin (35) of the present invention. As illustrated in FIG. 7, this embodiment illustrates a triangular shaped anchoring pin located along the shaft (7) of the tissue anchors. Tissue anchoring pins may further be located along the surface of the supporting sling of the present invention. The anchoring pins may be composed of biodegradable or non-biodegradable material. The elongated sharp pin tip of the anchoring device as illustrated in FIG. 7 allows the tissue anchor to be secured into tissues having different types of connective tissue such as fat, muscle, fascia and ligaments.

Figure 8:
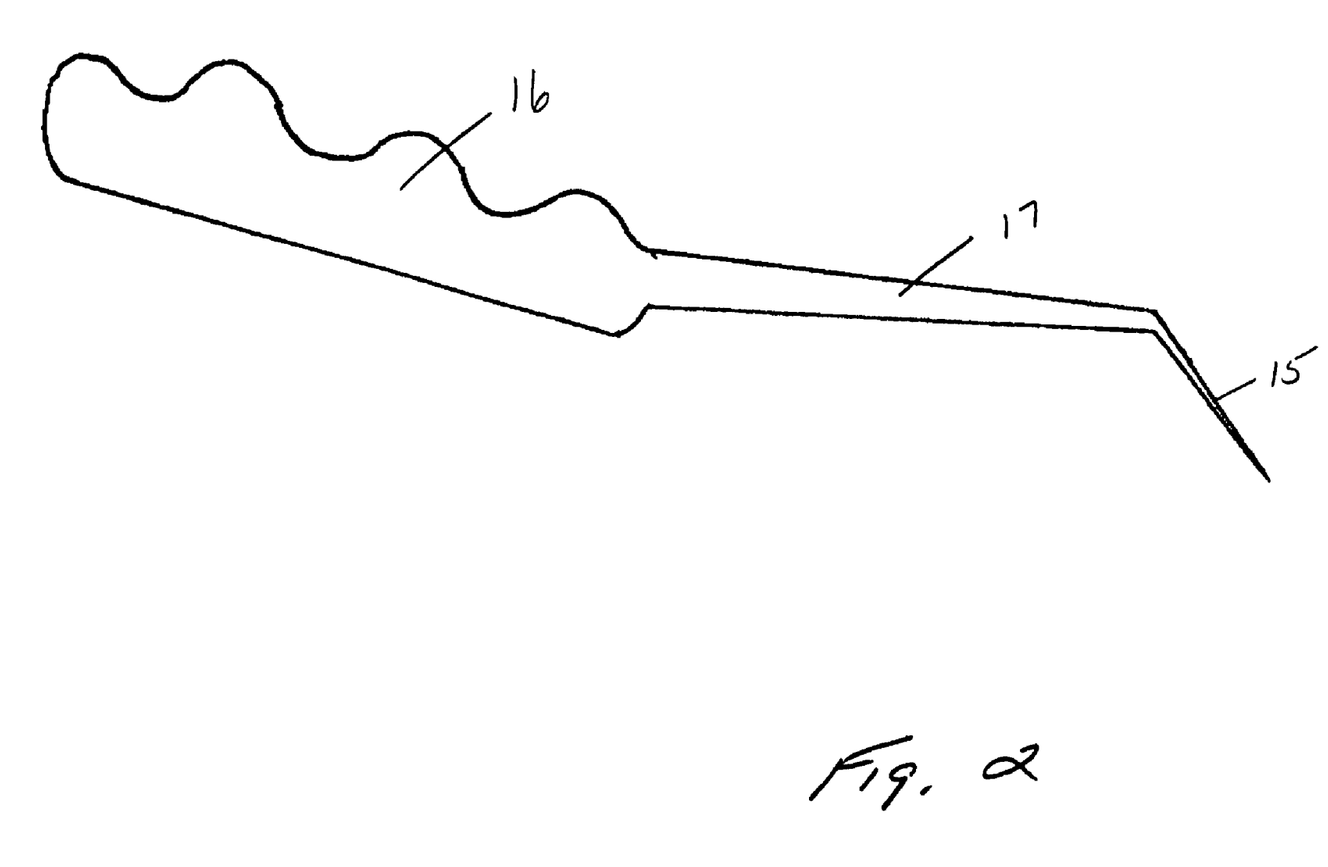
FIG. 8 is an illustration of an embodiment of the present invention's vaginal wall support sling with a suture attached to the tip of the sling with a hook placed at the end of the suture.

FIG. 8 discloses an alternative embodiment of the vaginal wall support sling with a suture (40) attached to the tip (41) of the sling and a hook (42) placed at the end of the suture. The embodiment of the sling illustrated in FIG. 8 can be positioned and practiced utilizing the sling transfer tools as discussed in association with FIGS. 2 and 3. In the embodiment of FIG. 8 the sling deployment tool is passed through the lower abdomen or through the obturator fossa. This embodiment as shown in FIG. 8 provides the anchoring pins (6) in the distal segment (10) of the body of the sling (9) with a suture extending from the tip of the sling and a transfer hook on the tip of the suture. As will be readily appreciated by those skilled in the art and an alternative embodiment of that illustrated in FIG. 8 would be a continuation of a distal segment of the sling to the sling transfer hook with or without a distinct tissue anchor segment located on the body of the supporting sling.

Figure 9:
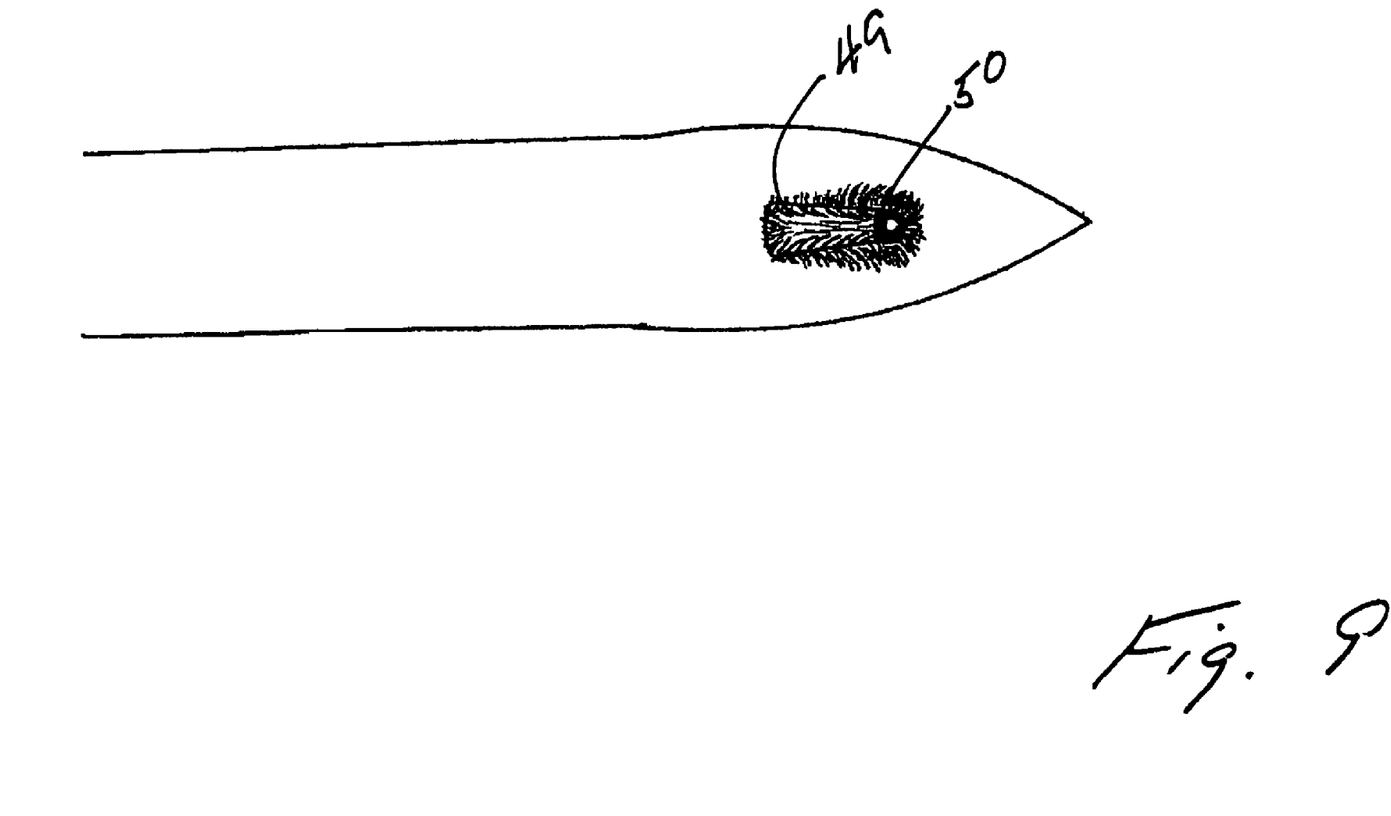
FIG. 9 is an illustration of an embodiment of the present invention's sling transfer instrument tip with groove and hole for transfer hook.

FIG. 9 illustrates an embodiment of the sling transfer instrument tip with a groove and hole for a transfer hook. As illustrated in FIG. 9, the tip of the instrument has a groove (49) and a hole (50) for a sling transfer hook. The groove (49) guides the hook into the hole (50) for easy engagement of the sling transfer instrument with the transfer hook. The shaft of the sling transfer instrument contemplates an embodiment for positioning through the lower abdomen or the obturator fossa.

Figure 10:
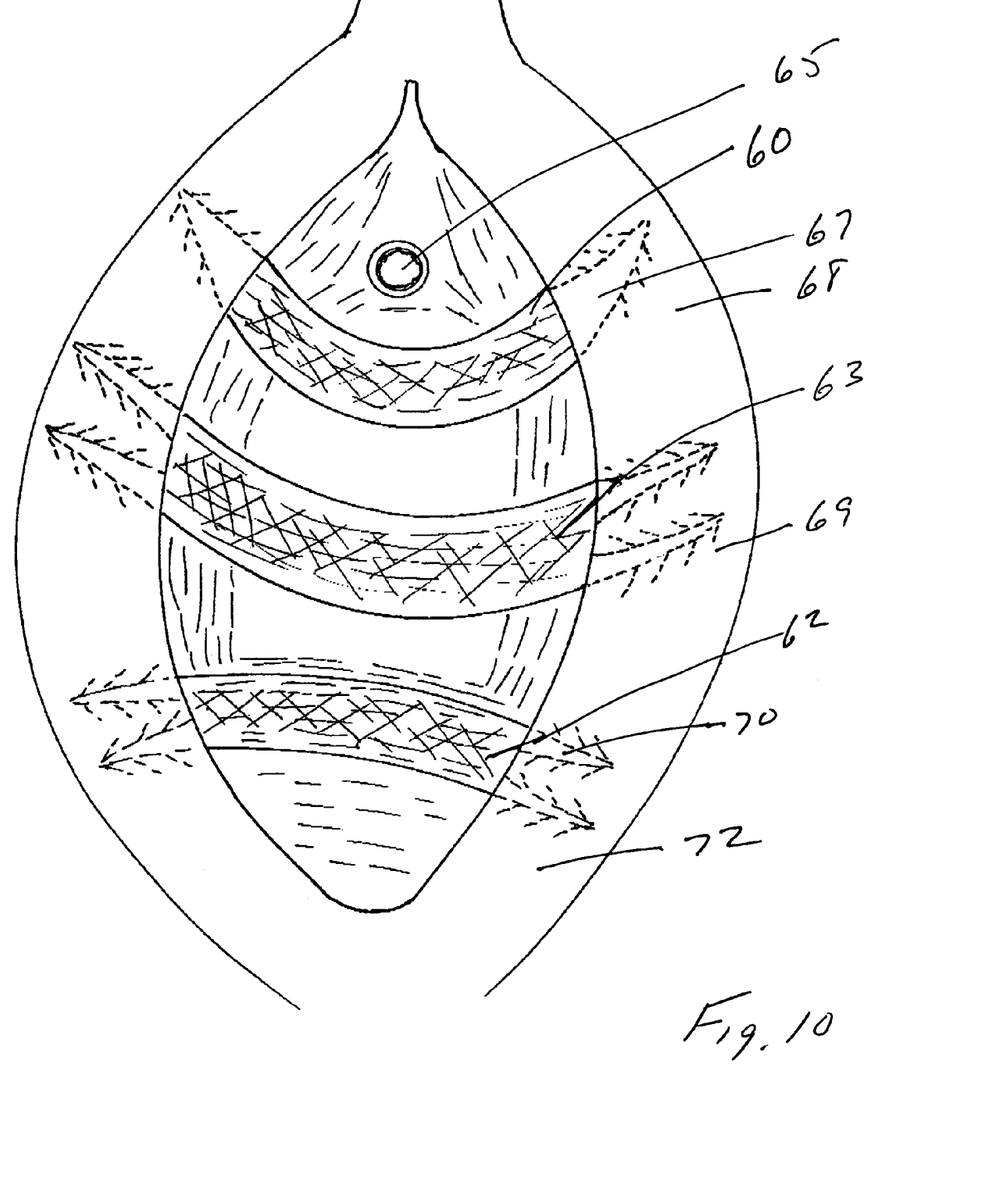
FIG. 10 is an illustration of an embodiment of the present invention's vaginal wall support sling positioned to support the urethra for surgical treatment of female stress urinary incontinence. The mid-vaginal and vaginal apex anterior vaginal support sling is positioned for surgical treatment of cystocele. The vaginal wall support sling positioned in the posterior vagina is placed for the surgical treatment of rectocele.

FIG. 10 illustrates the vaginal wall support sling (60) of the present invention positioned to support the urethra for surgical treatment of female stress urinary incontinence. In FIG. 10, a mid-vaginal and vaginal apex interior vaginal support sling is positioned for surgical treatment of cystocele. As illustrated, the vaginal wall support sling (62) positioned in the posterior vagina is positioned for the surgical treatment of rectocele. FIG. 10 further illustrates the vaginal wall support sling (60) positioned under the urethra (65) with tissue anchors (67) attached to durable fascia (68) of the pelvis for the surgical management of urinary incontinence in women. Also illustrated in FIG. 10, the interior vaginal wall support sling (63) is positioned with tissue anchors (70) attached to durable fascia (69) of the female pelvis for the surgical management of cystocele in women. The posterior vaginal wall support sling (62) is positioned with tissue anchors (70) attached to durable fascia (72) of the female pelvis for the surgical management of rectocele in women.

Figure 11:
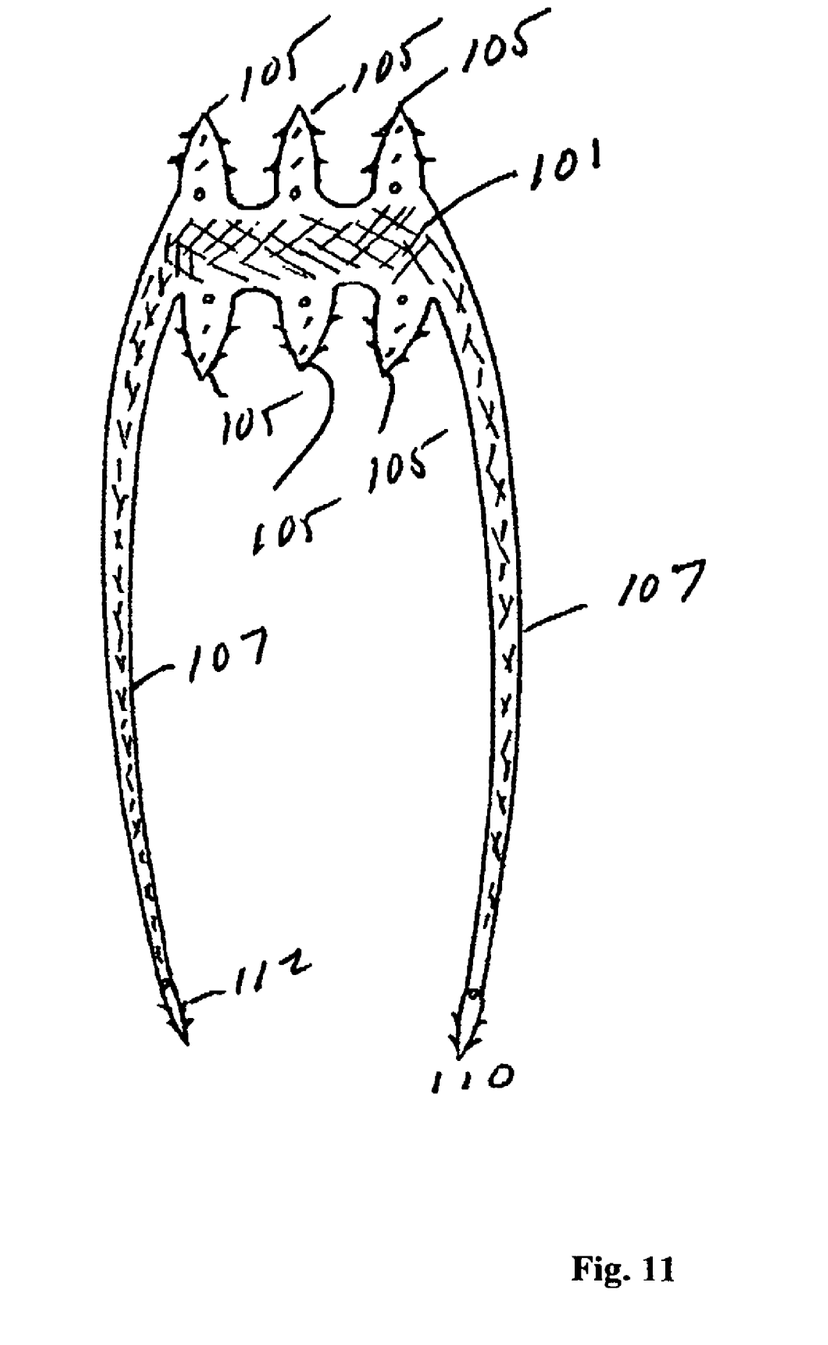
FIG. 11 is an illustration of an embodiment of the present invention's vaginal support sling anatomically positioned to augment the uterosacral ligament support of the vaginal apex.

FIG. 11 illustrates an embodiment of vaginal wall apical support sling with body of sling (101) that attaches to the vaginal wall apex, pericervical fascia, or any durable tissue of the vagina using multiple tissue anchors (105) that attach the body of the sling to the apex of the vagina. Each end (112) of the sling is attached to durable fascia and ligaments of the sacrum using tissue anchors. A sling limb (107) extends from the body of the sling to the tip of the sling (110) on each side. The limb of the sling (107) is anatomically positioned adjacent to the uterosacral ligaments to provide anatomical support for the apex of the vagina after hysterectomy and to the uterus prior to hysterectomy.

Figure 12:
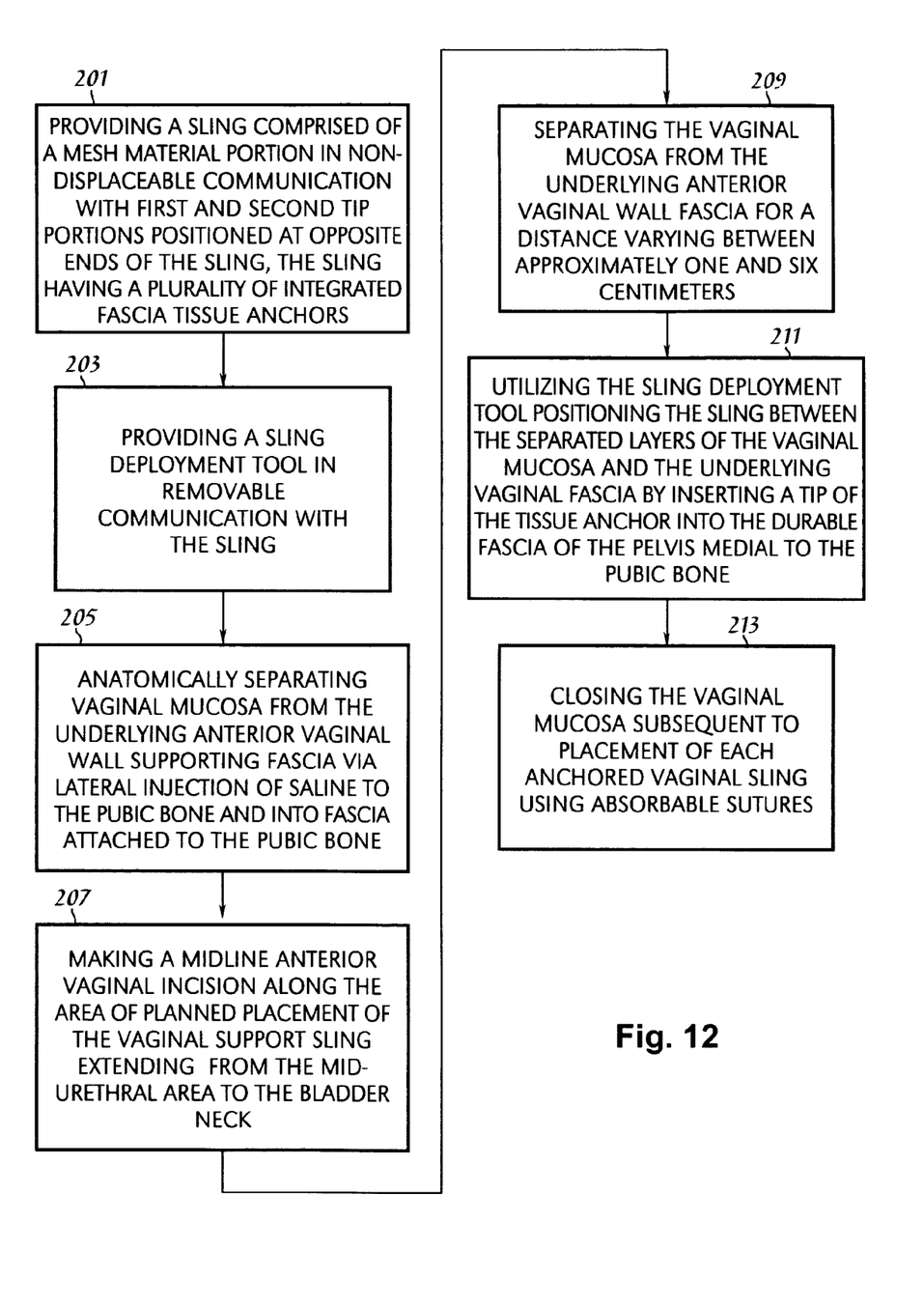
FIG. 12 is a non-limiting procedural sequence flow chart depicting one combination of the invention's deployment methodology.

Deployment of the vaginal sling and utilization of the deployment tools associated with the embodiments of the present invention proceed in accordance with the following procedure. It will be evident to those skilled in the art that the preferred sequence of surgical step technique is provided immediately hereafter for purposes of full and enabling disclosure.

A method for treating female pelvic prolapse comprising:

(a) providing a sling comprised of a mesh material portion in non-displaceable communication with first and second tip portions positioned at opposite ends of the sling, the sling having a plurality of integrated fascia tissue anchors;

(b) providing a sling deployment tool in removable communication with the sling;

(c) anatomically separating vaginal mucosa from the underlying anterior vaginal wall supporting fascia via lateral injection of saline to the pubic bone and into fascia attached to the pubic bone;

(d) making a midline anterior vaginal incision along the area of planned placement of the vaginal support sling extending from the mid-urethral area to the bladder neck;

(e) separating the vaginal mucosa from the underlying anterior vaginal wall fascia for a distance varying between approximately one and six centimeters.

(f) utilizing the sling deployment tool positioning the sling between the separated layers of the vaginal mucosa and the underlying vaginal fascia by inserting a tip of the tissue anchor into the durable fascia of the pelvis medial to the pubic bone; and, (g) closing the vaginal mucosa subsequent to placement of each anchored vaginal sling using absorbable sutures.

Although the invention has been described with reference to specific embodiments, and practice step sequences these descriptions are not meant to be construed in a limiting sense. Various modifications of the disclosed embodiments, as well as alternative embodiments of the invention and practice step sequences will become apparent to persons skilled in the art upon reference to the description of the invention. It should be appreciated by those skilled in the art that the conception and the specific embodiment and practice step sequences disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

What is claimed is:

1. A system for treating female pelvic prolapse comprising:
a sling comprised of a mesh material portion in non-displaceable communication with first and second tip portions positioned at opposite ends of the sling, the first and second tip portions having a plurality of integrated fascia tissue anchoring pins; and
a sling deployment tool in removable communication with the sling, wherein the sling deployment tool is utilized to position and insert the integrated fascia tissue anchors into durable fascia resulting in the sling's mesh material portion supporting mid and proximal urethral and bladder neck continence sites;
wherein a portion of the plurality of integrated fascia tissue anchoring pins pass through the mesh material portions of the sling.

2. The system of claim 1 wherein the durable fascia is selected from a group further comprising a pelvis, a pelvic fascia, ligaments attached to the pelvis, ligaments overlying the pelvis, and an urethropelvic ligament.

3. A system for treating female pelvic prolapse comprising:
a sling comprised of a mesh material portion in non-displaceable communication with first and second tip portions positioned at opposite ends of the sling, the first and second tip portions having a plurality of integrated fascia tissue anchoring pins; and
a sling deployment tool in removable communication with the sling, wherein the sling deployment tool is utilized to position and insert the integrated fascia tissue anchors into durable fascia resulting in the sling's mesh material portion supporting mid and proximal urethral and bladder neck continence sites;
wherein the sling's mesh portion is a multilayered mesh portion, wherein a portion of the plurality of integrated fascia tissue anchoring pins pass through the mesh material portion of the sling.

4. A system for treating female pelvic prolapse comprising:
a sling comprised of a mesh material portion in non-displaceable communication with first and second tip portions positioned at opposite ends of the sling, the sling having a plurality of integrated fascia tissue anchoring pins; and
a sling deployment tool in removable communication with the sling, wherein the sling deployment tool is utilized to position and insert the integrated fascia tissue anchors into durable fascia resulting in the sling's mesh material portion supporting mid and proximal urethral and bladder neck continence sites;
wherein each of the sling's anchoring pins portions are structured as essentially S-shaped structures.

5. A system for treating female pelvic prolapse comprising:
a sling comprised of a mesh material portion in non-displaceable communication with first and second tip portions positioned at opposite ends of the sling, the first and second tip portions having a plurality of integrated fascia tissue anchoring pins; and
a sling deployment tool in removable communication with the sling, wherein the sling deployment tool is utilized to position and insert the integrated fascia tissue anchors into durable fascia resulting in the sling's mesh material portion supporting mid and proximal urethral and bladder neck continence sites;
wherein the sling's tip portions comprise an inwardly slanted distal end, wherein the sling's tip portions further comprise a suture placed at the distal end of the sling's tip portions, wherein a portion of the plurality of integrated fascia tissue anchoring pins pass through the mesh material portion of the sling.

6. A system for treating female pelvic prolapse comprising:
a sling comprised of a mesh material portion in non-displaceable communication with first and second tip portions positioned at opposite ends of the sling, the first and second tip portions having a plurality of integrated fascia tissue anchoring pins; and
a sling deployment tool in removable communication with the sling, wherein the sling deployment tool is utilized to position and insert the integrated fascia tissue anchors into durable fascia resulting in the sling's mesh material portion supporting mid and proximal urethral and bladder neck continence sites;
wherein the sling's tip portions further comprise a suture and a sling transfer hook, wherein a portion of the plurality of integrated fascia tissue anchoring pins pass through the mesh material portion of the sling.

7. A method for treating female pelvic prolapse comprising:
(a) providing a sling comprised of a mesh material portion in non-displaceable communication with first and second tip portions positioned at opposite ends of the sling, the sling having a plurality of integrated fascia tissue anchors;
(b) providing a sling deployment tool in removable communication with the sling;
(c) anatomically separating vaginal mucosa from an underlying anterior vaginal wall supporting fascia via lateral injection of saline to a pubic bone and into fascia attached to the pubic bone;
(d) making a midline anterior vaginal incision along an area of planned placement of a vaginal support sling extending from a mid-urethral area to a bladder neck;
(e) separating the vaginal mucosa from the underlying anterior vaginal wall supporting fascia for a distance varying between one centimeter and six centimeters;
(f) utilizing the sling deployment tool positioning the sling between separated layers of the vaginal mucosa and an underlying vaginal fascia by inserting a tip of the tissue anchor into a durable fascia of a pelvis medial to the pubic bone; and,
(g) closing the vaginal mucosa subsequent to placement of each anchored vaginal sling using absorbable sutures.

8. The method for treating female pelvic prolapse according to claim 7 wherein the sling deployment tool is used to place the sling into the durable fascia of the pelvis medial to the pelvis.

9. A sling for treating female pelvic prolapse comprising:
a sling comprised of a mesh material portion in non-displaceable communication with first and second tip portions positioned at opposite ends of the sling, the first and second tip portions having a plurality of integrated fascia tissue anchors; and
a sling deployment tool in removable communication with the sling, wherein the sling deployment tool is utilized to position and insert the integrated fascia tissue anchors into durable fascia resulting in the sling's mesh material portion simultaneously supporting mid and proximal urethral and bladder neck continence sites;
wherein a portion of the plurality of integrated fascia tissue anchors pass through the mesh material of the sling.

10. A sling for treating female pelvic prolapse comprising:
a sling comprised of a mesh material portion in non-displaceable communication with first and second tip portions positioned at opposite ends of the sling, the first and second tip portions having a plurality of integrated fascia tissue anchors; and
a sling deployment tool in removable communication with the sling, wherein the sling deployment tool is utilized to position and insert the integrated fascia tissue anchors into durable fascia resulting in the sling's mesh material portion simultaneously supporting mid and proximal urethral and bladder neck continence sites;
wherein the sling's mesh portion is a multilayered mesh portion, wherein a portion of the plurality of integrated fascia tissue anchors pass through the mesh material portion of the sling.

11. A sling for treating female pelvic prolapse comprising:
a sling comprised of a mesh material portion in non-displaceable communication with first and second tip portions positioned at opposite ends of the sling, the sling having a plurality of integrated fascia tissue anchors; and
a sling deployment tool in removable communication with the sling, wherein the sling deployment tool is utilized to position and insert the integrated fascia tissue anchors into durable fascia resulting in the sling's mesh material portion simultaneously supporting mid and proximal urethral and bladder neck continence sites;
wherein each of the sling's anchoring pins portions are structured as essentially S-shaped structures.

12. A sling for treating female pelvic prolapse comprising:
a sling comprised of a mesh material portion in non-displaceable communication with first and second tip portions positioned at opposite ends of the sling, the first and second tip portions having a plurality of integrated fascia tissue anchors; and
a sling deployment tool in removable communication with the sling, wherein the sling deployment tool is utilized to position and insert the integrated fascia tissue anchors into durable fascia resulting in the sling's mesh material portion simultaneously supporting mid and proximal urethral and bladder neck continence sites;
wherein the sling's tip portions comprise an inwardly slanted distal end, wherein the sling's tip portions further comprise a suture placed at the distal end of the sling's tip portions, wherein a portion of the plurality of integrated fascia tissue anchors pass through the mesh material portion of the sling.

13. A sling for treating female pelvic prolapse comprising:
a sling comprised of a mesh material portion in non-displaceable communication with first and second tip portions positioned at opposite ends of the sling, the first and second tip portions having a plurality of integrated fascia tissue anchors; and
a sling deployment tool in removable communication with the sling, wherein the sling deployment tool is utilized to position and insert the integrated fascia tissue anchors into durable fascia resulting in the sling's mesh material portion simultaneously supporting mid and proximal urethral and bladder neck continence sites;
wherein the sling's tip portions further comprise a suture and a sling transfer hook, wherein a portion of the plurality of integrated fascia tissue anchors pass through the mesh material portion of the sling.

* * * * *